US00PP29621P3

(12) United States Plant Patent
Danziger

(10) Patent No.: US PP29,621 P3
(45) Date of Patent: Aug. 21, 2018

(54) ***SCABIOSA* PLANT NAMED 'DCANDYSCOP'**

(50) Latin Name: *Scabiosa atropurpurea*
Varietal Denomination: DCANDYSCOP

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 37 days.

(21) Appl. No.: 15/330,252

(22) Filed: Aug. 29, 2016

(65) Prior Publication Data

US 2018/0064019 P1 Mar. 1, 2018

(51) Int. Cl.
*A01H 5/02* (2018.01)

(52) U.S. Cl.
USPC ..... Plt./478
CPC ..... *A01H 5/025* (2013.01)

(58) Field of Classification Search
USPC ..... Plt./478
See application file for complete search history.

*Primary Examiner* — Keith O Robinson
(74) *Attorney, Agent, or Firm* — Cassandra Bright

(57) ABSTRACT

A new and distinct *Scabiosa* cultivar named 'DCANDYSCOP' is disclosed, characterized by clear pink flowers, long peduncles and many flowering stems per plant. The new variety is a *Scabiosa*, suitable for cut flower production and outdoor garden or container uses.

2 Drawing Sheets

Figure 1:
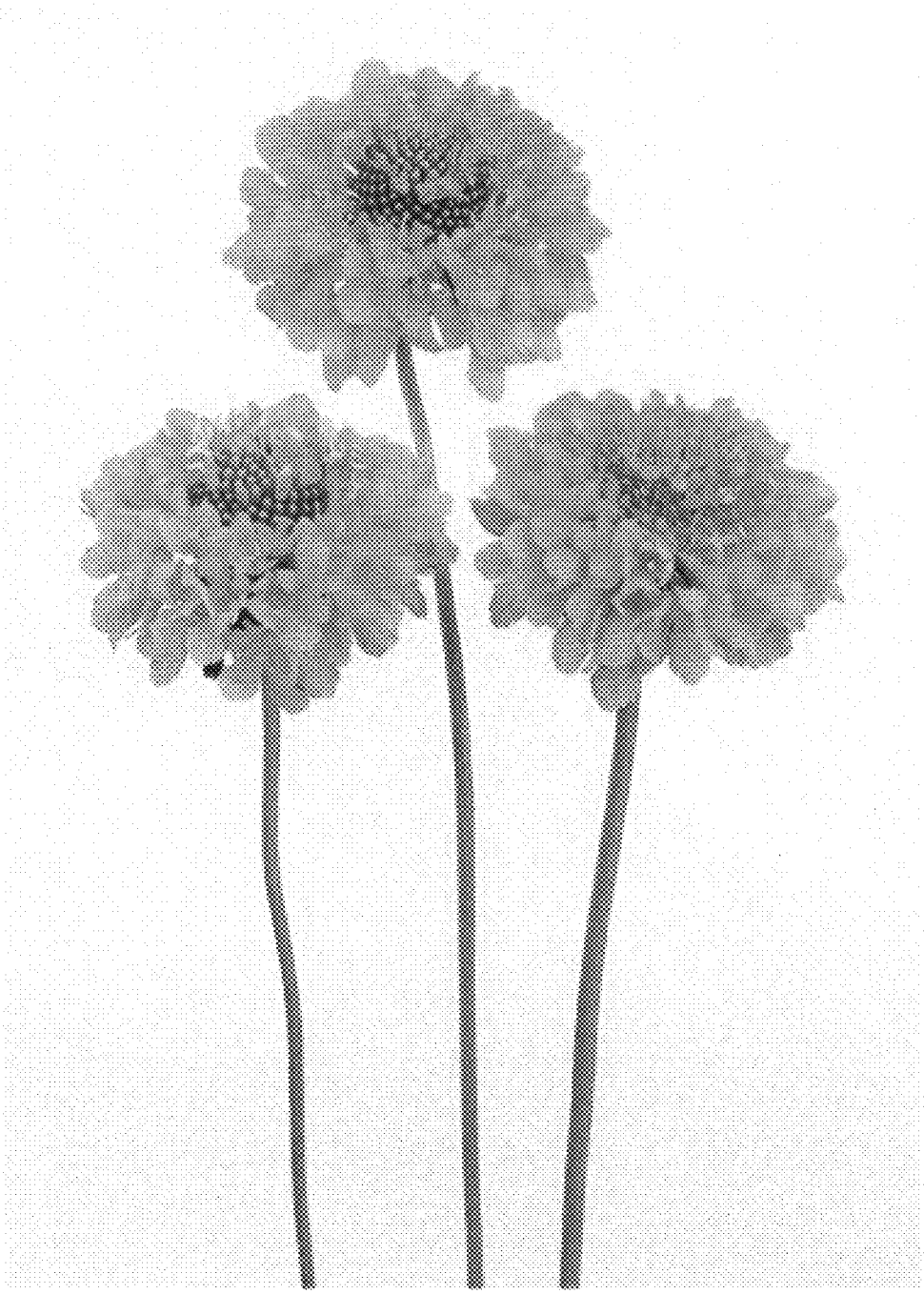

Latin name of the genus and species: *Scabiosa atropurpurea.*

Variety denomination: 'DCANDYSCOP'.

BACKGROUND OF THE INVENTION

The new *Scabiosa* cultivar is a product of a planned breeding program conducted by the inventor, Gavriel Danziger in Moshav Mishmar Hashiva, Israel. The objective of the breeding program was to produce new *Scabiosa* varieties with long flower stems and strong flowering necks. The open pollination resulting in this new variety was made during the Summer of 2012.

The seed parent is the unpatented, propriety variety referred to as *Scabiosa* 'SB 12-776'. The pollen parent is unknown as it was an open pollination breeding program. The new variety was discovered in Spring of 2013 by the inventor in a group of seedlings resulting from the 2012 open pollination, in a greenhouse in Moshav Mishmar Hashiva, Israel.

Asexual reproduction of the new cultivar 'DCANDYSCOP' was first performed by basal vegetative cuttings during April of 2012, at a greenhouse in Moshav Mishmar Hashiva, Israel. Subsequent propagation has shown that the unique features of this cultivar are stable and reproduced true to type in multiple successive generations.

SUMMARY OF THE INVENTION

The cultivar 'DCANDYSCOP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCANDYSCOP'. These characteristics in combination distinguish 'DCANDYSCOP' as a new and distinct *Scabiosa* cultivar:

1. Clear pink flower color.
2. Long peduncle.

3. Many flowering stems per plant.
4. Suitability for cut flower production.

PARENT COMPARISON

Plants of the new cultivar 'DCANDYSCOP' are similar to plants of the seed parent, in most horticultural characteristics, however, plants of the new cultivar 'DCANDYSCOP' differ in the following;

1. Peduncle length of the new variety is longer than that of the parent.
2. New variety produces a larger flower than the seed parent.
3. Peduncle diameter of the new variety is longer than that of the parent.

COMMERCIAL COMPARISON

Plants of the new cultivar 'DCANDYSCOP' can be compared to the commercial variety *Scabiosa* 'DVANILSCOP', patent application Ser. No. 15/330,251, filed concurrently. These varieties are similar in most horticultural characteristics; however, 'DCANDYSCOP' differs in the following:

1. 'DCANDYSCOP' has a pink flower, this comparator has a white flower.
2. 'DCANDYSCOP' produces more inflorescence per plant than this comparator.
3. Peduncles of 'DCANDYSCOP' are shorter than peduncles of this comparator.

Plants of the new cultivar 'DCANDYSCOP' can also be compared to the variety *Scabiosa* 'DBLCKBRY', unpatented. These varieties are similar in most horticultural characteristics; however, 'DCANDYSCOP' differs in the following:

1. Flowers of 'DCANDYSCOP' are pink, this comparator has a dark purple flower.
2. 'DCANDYSCOP' produces more inflorescence per plant than this comparator.

3. Under hot temperatures plants of 'DCANDYSCOP' produce better quality inflorescence than this comparator in the same conditions.

BRIEF DESCRIPTION OF THE PHOTOGRAPHS

The accompanying photograph in FIG. 1 illustrates in full color multiple inflorescence of 'DCANDYSCOP' grown outdoors in Moshav Mishmar Hashiva, Israel.

Figure 2:
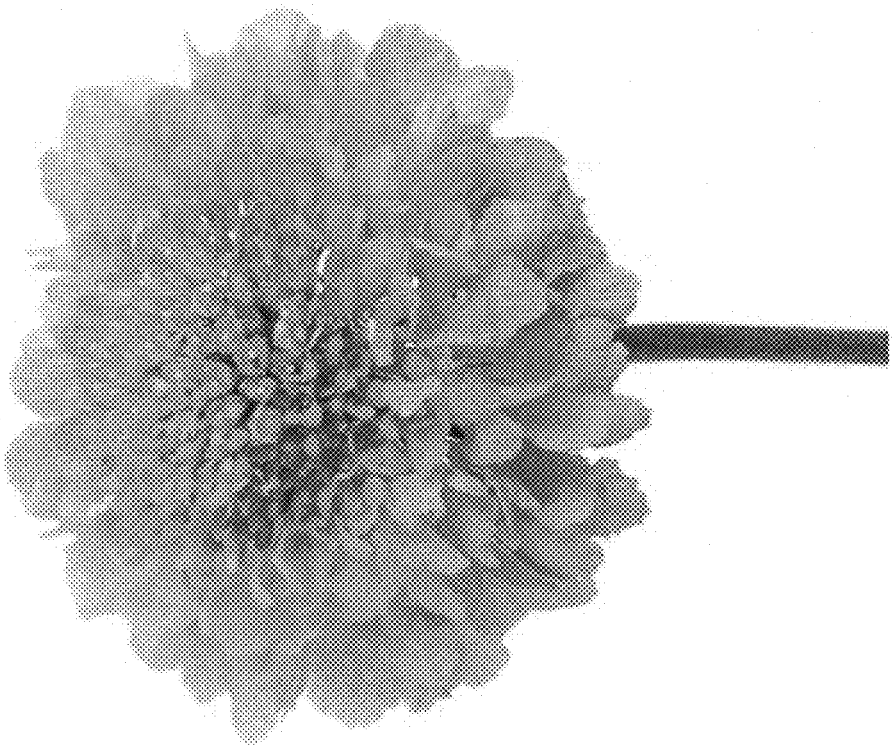

FIG. 2 illustrates in full color a typical inflorescence of 'DCANDYSCOP'. Photos were taken of flowers approximately 3 days after harvest, from plants of approximately 9 months of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCANDYSCOP' plants grown in ground beds, outdoors in Moshav Mishmar Hashiva, Israel, under natural lighting. Measurements were taken during April of 2016. The plants were approximately 6 months old. The growing temperature ranged from approximately 12° C. to 35° C. during the days, 4° C. to 28° C. during the nights. Measurements and numerical values represent averages of typical plant types.

Botanical classification: *Scabiosa atropurpurea* 'DCANDYSCOP'.

PROPAGATION

Time to initiate rooting: About 14 days at approximately 23° C.

Root description: Fine, tufted roots. Brown to light brown, not accurately measured with R.H.S. chart.

PLANT

Growth habit: Perennial with a mounded base, producing straight, upright flowering stems.

Height: Approximately 80 cm to top of foliage. Approximately 128 cm top of flowering plane.

Plant spread: Approximately 30 cm.

Growth rate: Moderate.

Characteristics of primary lateral branches:

- *Length of primary stems*.—Approximately 80 cm, then stem becomes peduncle.
- *Diameter*.—Approximately 1.0 cm.
- *Color*.—Near Yellow-Green 144C.
- *Texture*.—Glabrous.
- *Strength*.—Strong.

Number of leaves per lateral branch: Approximately 12 sets of leaves.

FOLIAGE

Leaf:

- *Arrangement*.—Opposite.
- *Average length*.—Approximately 15.0 cm.
- *Average width*.—Approximately 4.0 cm.
- *Shape of blade*.—Lyrate.
- *Apex*.—Mucronate, bristle-like appendage.
- *Base*.—Wedge shaped.
- *Attachment*.—Petiolate.
- *Margin*.—Deeply crenate.
- *Texture of top surface*.—Canescent.
- *Texture of bottom surface*.—Canescent.
- *Appearance top surface*.—Matte.
- *Appearance bottom surface*.—Matte.
- *Leaf internode length*.—Average 3-5 mm.
- *Color*.—Young foliage upper side: Near Green 137B. Young foliage under side: Near Green 137B. Mature foliage upper side: Near Yellow-Green 146B. Mature foliage under side: Near Yellow-Green 146B.
- *Venation*.—Type: Cross venulate. Venation color upper side: Near Green N137B. Venation color under side: Near Green 137B.

Petiole:

- *Length*.—About 3.5 cm.
- *Diameter*.—About 0.6 cm.
- *Pubescence*.—Pilose.
- *Color*.—Near Green 137B.

FLOWER

Natural flowering season: Spring and Summer.

Time to flowering from rooted cutting: Approximately 12 weeks.

Inflorescence and flower type and habit: Terminal composite inflorescence, round, with numerous complete flowers. Outer flowers larger than the inner flowers. Approximately 100 to 300 flowers per inflorescence.

Rate of flower opening: Approximately 3 weeks from bud to fully opened flower.

Inflorescence longevity on plant: At least 3 weeks before any significant change is observed.

Vase life: Approximately 14 days.

Approximate quantity of flowers per plant: Approximately 10 mature inflorescence, showing color and 7 immature, completely green inflorescence per plant.

Bud:

- *Bud shape*.—Sphere.
- *Bud length*.—Approximately 1.4 cm.
- *Bud diameter*.—Approximately 2.4 cm.
- *Bud color*.—Near Red 51C.

Inflorescence:

- *Diameter of entire inflorescence*.—Approximately 10 cm.
- *Depth of inflorescence*.—Approximately 0.8 cm.
- *Inner cushion diameter*.—Approximately 1.3 cm.
- *Receptacle shape*.—Round.
- *Receptacle height*.—Average 1.2 cm.
- *Receptacle diameter*.—Average 1.2 cm.
- *Receptacle color*.—Near Yellow-Green 145D.

Individual flower bud:

- *Shape*.—Round.
- *Length*.—Approximately 1.1 cm.
- *Diameter*.—Approximately 0.4 cm.
- *Color*.—Near Red 51C.

Large outer flowers:

- *Flower length*.—About 2.8 cm.
- *Flower width*.—About 1.5 cm.
- *Upper petals* (*upper lip*).—Number: 4. Length: About 5 to 7 mm. Width: About 4 mm. Shape: Upper surface: Napiform. Lower surface: Napiform. Margin: Entire, lightly wavy. Texture: Glabrous, all surfaces. Color: When opening: Upper surface: Near Red 55A. Lower surface: Near Red 54C. Fully opened: Upper surface: Near Red 55A. Lower surface: Near Red 56B.

*Lower petals* (*lower lip*).—Quantity: 1. Length: About 0.8 cm. Width: About 0.6 cm. Shape: Napiform. Apex shape: Retuse. Color: When opening: Upper surface: Near Red 55B. Lower surface: Near Red 54C. Fully opened: Upper surface: Near Red 55D. Lower surface: Near Red 56D.

*Throat*.—Length: Approximately 1.0 cm. Width: Approximately 0.3 cm. Texture: Glabrous. Color: Near Red 56A.

*Bracteole*.—Quantity: 2 per flower. Length: Average 0.2 mm. Diameter: Approximately 0.1 mm. Shape: Linear, hair-like. Texture: Glabrous, upper and lower surfaces. Color: Near Green 142D.

Smaller inner flowers:

*Flower length*.—0.9 cm.

*Flower width*.—0.3 cm.

*Upper petals* (*upper lip*).—Number: 3. Length: 0.1 cm. Width: 0.1 cm. Shape: Broad ovate. Margin: Entire, lightly wavy. Texture: Upper surface: Glabrous. Lower surface: Glabrous. Color: When opening: Upper surface: Near Red 45A. Lower surface: Near Red 45B. Fully opened: Upper surface: Near Red 54A. Lower surface: Near Red 54C.

*Lower petals* (*lower lip*).—Quantity: 1. Length: About 2 mm. Width: About 1 mm. Shape: Broad ovate. Apex shape: Obtuse. When opening: Color: When opening: Upper surface: Near Red 46A. Lower surface: Near Red 54C. Fully opened: Upper surface: Near Red 51A. Lower surface: Near Red 54D.

*Throat*.—Length: About 9 mm. Width: About 2.5 mm. Texture: Upper surface: Glabrous. Lower surface: Glabrous. Color: Near Red 54D.

*Bracteole*.—Quantity: 2 per flower. Length: Average 0.2 mm. Diameter: About 0.1 mm. Shape: Linear, hair-like. Texture: Glabrous, upper and lower surfaces. Color: Near Green 142D.

Phyllaries/involucral bracts:

*Quantity per inflorescence*.—Average 20.

*Shape*.—Falcate.

*Length*.—Average 0.4 to 1.2 cm.

*Width*.—Approximately 3 mm.

*Apex*.—Acute.

*Base*.—Truncate.

*Margin*.—Entire.

*Texture*.—Upper surface: Glabrous. Lower surface: Glabrous.

*Color*.—Upper Surface: Near Green N137A. Lower Surface: Near Green 137A.

Peduncle:

*Length*.—Longest average 50 cm. Shortest average 12 cm.

*Diameter*.—Approximately 0.5 cm.

*Texture*.—Glabrous.

*Color*.—Near Yellow-Green 1546B.

*Orientation*.—Approximately 180 degree angle from stem.

*Strength*.—Strong.

Pedicel: None.

Fragrance: None detected.

REPRODUCTIVE ORGANS

Reproductive organs identical in both size flowers.

Stamens:

*Number*.—4.

*Filament length*.—Approximately 1.3 cm.

Anthers:

*Length*.—Approximately 0.2 cm.

*Shape*.—Rectangle.

*Color*.—Near White 155D.

*Pollen*.—Color: Near White 155D RHS. Quantity: Scarce.

Pistil:

*Number*.—1.

*Length*.—Approximately 1.5 cm.

*Style*.—Length: Approximately 0.1 mm. Color: Near White 155D.

*Stigma*.—Shape: Lobed. Color: Near White 155D.

OTHER CHARACTERISTICS

Seeds and fruits: Not observed.

Disease/pest resistance: Neither resistant nor susceptibility to normal diseases and pests of *Scabiosa* has been observed.

Temperature tolerance: USDA zones 3-9.

What is claimed is:

1. A new and distinct cultivar of *Scabiosa* plant named 'DCANDYSCOP' as herein illustrated and described.

* * * * *